United States Patent [19]

Schuy

[11] Patent Number: 5,360,717
[45] Date of Patent: Nov. 1, 1994

[54] AGENT, FOR IMMUNOCHEMICAL ASSAYS, CONTAINING AMINE OXIDES

[75] Inventor: Wilhelm Schuy, Obererbach, Germany

[73] Assignee: Behringwerke Aktiengesellschaft, Marburg/Lahn, Germany

[21] Appl. No.: 938,591

[22] Filed: Sep. 3, 1992

Related U.S. Application Data

[63] Continuation of Ser. No. 807,618, Dec. 13, 1991, abandoned, which is a continuation of Ser. No. 319,206, Mar. 6, 1989, abandoned.

[30] Foreign Application Priority Data

Mar. 8, 1988 [DE] Germany ............................ 3807478

[51] Int. Cl.$^5$ .......................................... G01N 33/543
[52] U.S. Cl. ................... 435/7.94; 435/7.1; 435/962; 436/501; 436/518; 436/826
[58] Field of Search ............ 435/7.1, 7.94, 962, 435/970, 805; 436/501, 518, 810, 826

[56] References Cited

U.S. PATENT DOCUMENTS

| | | | |
|---|---|---|---|
| 4,248,862 | 2/1981 | Ellwood et al. | 436/297 X |
| 4,279,993 | 7/1981 | Magers et al. | 436/527 X |
| 4,597,975 | 7/1986 | woodward et al. | |
| 4,639,425 | 1/1987 | Baier | 436/533 X |
| 4,659,565 | 4/1987 | Smith et al. | 564/297 |

FOREIGN PATENT DOCUMENTS

| | | | |
|---|---|---|---|
| 0747963 | 12/1966 | Canada | 260/583 D |
| 0132948 | 2/1985 | European Pat. Off. | |
| 0133272 | 2/1985 | European Pat. Off. | |
| 0215457 | 12/1986 | European Pat. Off. | |

OTHER PUBLICATIONS

European Search Report for European Patent No. 0,215,457.

Suguira et al., Japanese Kokai Patent No. 83–187862, Published Nov. 2, 1983, English Translation.

*Primary Examiner*—Mary E. Ceperley
*Attorney, Agent, or Firm*—Finnegan, Henderson, Farabow, Garrett & Dunner

[57] ABSTRACT

Amine oxide-containing agents for immunochemical assays are described.

The amine oxides are contained in constituents of agents for such assays which are used for receiving samples. The amine oxides are also contained in those constituents of the agent in which the immunochemical reaction takes place. The amine oxides bring about an improvement of the assay result, i.e., they increase the sensitivity of the detection and of the determination of an analyte contained in biological material.

9 Claims, No Drawings

AGENT, FOR IMMUNOCHEMICAL ASSAYS, CONTAINING AMINE OXIDES

This application is a continuation of prior application Ser. No. 07/807,618, filed Dec. 13, 1991, abandoned which was itself a continuation under 37 CFR 1.62 of prior application Ser. No. 07/319,206, filed Mar. 6, 1989, abandoned.

The invention relates to an agent for immunochemical detection and for the determination of an analyte in a biological material, this agent containing an amine oxide.

Known immunochemical assay systems involve the addition of proteins, polysaccharides and/or surfactants which do not participate in the immunochemical reaction but are suitable for favorably influencing the result of such a reaction.

German Offenlegungsschrift 3,638,767 describes an incubation medium for solid-phase immunochemical assays which contains lactoferrin, fetal calf serum, polyoxyethylene (20) sorbitan monolaurate (®Tween 20) and buffer salts.

EP-A 215,457 also describes additions of surfactants from the group of the poloxamers, for example ®Pluronic F 68 and from the group of the poloxamines, for example TM Tetronic 707 and 1107, the three mentioned compounds being emphasized as advantageous compared with ®Tween 20.

Surprisingly, it has been found that amine oxides are even more suitable to favorably influence an immunochemical reaction, which brings about greater sensitivity of the detection and of the determination of an analyte contained in a biological material which can also be called a sample.

Furthermore, it has been found that amine oxides as a constituent of such an agent are particularly suitable for the preparation of the sample for the assay.

The invention thus relates to an agent, for the detection or for the determination of an analyte in a biological material, containing an amine oxide of the formula I

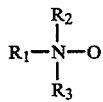

where a)

$R_1$ are 1-alkanoyl groups or 1-alkenoyl-amino-propyl groups where the alkanoyl radicals or alkenoyl radicals contain 8–18 carbon atoms or their mixtures and
$R_2$ and $R_3$ are methyl groups, ethyl groups or propyl groups or their mixtures, or b)

$R_1$ is alkanyl groups or alkenyl groups having 8 to 18 carbon atoms or their mixtures and
$R_2$ and $R_3$ are methyl groups, ethyl groups or propyl groups or their mixtures, or c)

$R_1$ is alkanyl groups or alkenyl groups having 8 to 18 carbon atoms or their mixtures,
$R_2$ is methyl, ethyl or propyl and
$R_3$ is hydroxyethyl or hydroxypropyl or their mixtures, or d)

$R_1$ is alkanyl groups or alkenyl groups having 8 to 18 carbon atoms or their mixtures and
$R_2$ and $R_3$ are hydroxyethyl or hydroxypropyl, or e)

$R_1$ is alkanyl groups or alkenyl groups having 8 to 18 carbon atoms or their mixtures and oxyethyl or oxypropyl or their polycondensates,
$R_2$ and $R_3$ are methyl, ethyl, propyl or hydroxyethyl or hydroxypropyl or mixtures thereof, or f)

$R_1$ is alkanoyl groups or alkenoyl groups having 8–18 carbon atoms or their mixtures and oxyethyl or oxypropyl or their polycondensates,
$R_2$ and $R_3$ are methyl, ethyl, propyl or hydroxyethyl or hydroxypropyl or mixtures thereof where $R_1$, $R_2$ and $R_3$ may contain amido groups or phenol radicals, and immunochemical reactants, of which at least one can react with the analyte, and where these reactants may likewise be present on or in this agent, or some of them, or all, can be present on or in a further agent.

A large number of agents containing immunochemical reactants and/or bioaffinity binding partners are known.

In general, the agents are named after the immunochemical processes for which they are used.

Agents within the meaning of the invention are those with which precipitates are produced as a dispersion or in a gel, or agglutinates of particles are produced, or their absence is brought about, or those in which a color signal or a radiation is produced or prevented by the immunochemical reaction.

Preferred agents from the last-mentioned group are those with which solid-phase immunochemical assays are carried out, which are called ELISA (enzyme-linked immunosorbent assay) or scintillation assay when a coloration or a radiation is produced from an enzyme substrate, solid-phase radioimmunoassay when a radiation is produced by a radio-active-labeled isotope, or solid-phase fluorescence assay when a fluorescence is produced by a fluorogen.

Diagnostic agents contain antigen, antibody or a combination of both as reactants, as well as other binding partners having bioaffinity to the reactants or the analyte, for example lectins, complement, protein A or G, and also derivatized biotin and avidin, where at least one of the reactants can be labeled, and if appropriate reagents for detecting the label. Moreover, one of the reactants may be present as solid phase.

A solid phase within the meaning of the invention is a water-insoluble carrier to which one or more reactants is bound.

Examples of carriers are latex particles, granular, swellable or non-swellable material, spheres, the insides of tubes, multi-well plates as particular embodiment of an arrangement of tubes, and also porous materials which may be called an absorbent matrix.

A device for receiving a sample, for example a vessel for receiving samples or the receiving zone for the sample, for example an absorbent matrix, on a so-called "dry-chemical" assay system, can be a constituent of the agent according to the invention. Alternatively, an aqueous solution also containing buffer salts and if appropriate stabilizing additions such as proteins or polysaccharides as likewise analyte-stabilizing substances can be the constituent, where the amine oxide is contained in a concentration of 2–80 g/l, preferably of 5–50 g/l, particularly preferably of 10–40 g/l.

The amine oxide can also be contained in a device in which the immunochemical reaction takes place, as a constituent of the diagnostic agent.

Examples of the biological materials which are also called the sample and which contain the analyte are tissues of biopsies or autopsies, blood cells, serum or plasma, secreta, liquor, blood from inflamed and non-inflamed tissue, accidental products of tissue, and metabolic excretions.

The invention furthermore relates to a process for the immunochemical determination of an analyte contained in a biological material, which comprises combining the analyte with an amine oxide, if appropriate in an aqueous solution, and carrying out an immunochemical determination on the resultant mixture.

The invention furthermore relates to the use of an amine oxide in immunochemical assays.

The biological materials are combined with the amine oxide and can be stored in this manner for a relatively long time without the analyte contained in the mixture changing with respect to its immunochemical properties.

The biological materials can also be suspended and/or dissolved in an aqueous solution containing the amine oxide, and/or they can be diluted with such a solution, and stored in this state for a relatively long time. In the suspended, dissolved and/or diluted state they are employed without further treatment in the immunochemical detection or the immunochemical determination of the analyte. On mixing with viscous sample material such as sputum, amine oxide-containing aqueous solutions have the advantageous property that they liquefy this sample material more rapidly than aqueous solutions of acetylcystein and pancreatin, solutions which had already been used for liquefying mucus, and the sample material can thus be more easily pipetted.

Preferred immunochemical processes are those in which one of the reactants is present in solid phase, where the treated material described as above is combined with the solid phase, if appropriate together with other immunochemical reactants besides those of the solid phase and reagents for the detection of the analyte, where the solid phase is subsequently separated from the liquid phase, and the analyte is determined either on the solid or in the liquid phase.

EXAMPLE 1

The following compounds were dissolved in a phosphate-buffered sodium chloride solution (PBS), pH 7.2, containing 7.25 mmol/l Na$_2$HPO$_4$, 2.72 mmol/l KH$_2$PO$_4$, 140 mmol/l NaCl and 3 mmol/l NAN$_3$, in concentrations of 10 g/l (a) and 40 g/l (b) (in the table, they are referred to as additions):

amine oxide WS 35, a product by Messrs. Goldschmidt, which is a 1-alkoylamino-3-dimethylamino-propane-3-N-oxide where the alkoyl radical is derived from a mixture of fatty acids having chain lengths of from C$_8$ to C$_{18}$;

coconut dimethylamine oxide of the formula

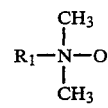

where R$_1$ is alkyl radicals obtained from the coconut fat, i.e. having chain lengths of from C$_8$ to C$_{18}$;

tetradecyldimethylamine oxide;

coconut-bis-(2-hydroxyethyl)-amine oxide, where coconut is alkyl radicals which have been obtained from coconut fat and have chain lengths of from C$_8$ to C$_{18}$;

®Pluronic F 68, commercial name of a compound from the group of the poloxamers or ®Tetronic 707 and Tetronic 1107, commercial names of compounds from the group of the poloxamines (addition products of ethylene oxide and propylene oxide on ethylenediamine).

6 µl aliquots of a pool of Herpes simplex virus (HSV)-containing pustule liquid were each mixed with 1.2 ml of the previously described solutions. The resultant samples were stored at 20°–25° C. up to 21 days.

150 µl were sampled on days 0, 7, 14 and 21, and HSV determination was carried out.

The determination was carried out following the solid phase double-sided immunochemical process (sandwich ELISA). The following materials were prepared for this ELISA:

1.1 Multiwell plates, coated with antibodies against HSV 1 and 2

Multiwell plates, i.e. round-bottom immunoplates II 96 F (made by Nunc, Roskilde, Denmark, article No. 262162) were coated with goat anti-HSV 1 and 2 immunoglobulin G (IgG). For this purpose, the IgG was diluted to 20 mg/l in 100 mmol/l of sodium bicarbonate, pH 9.6. 100 µl of the dilution were transferred into each well of the multiwell plates. The assay plates which had been filled in this manner were allowed to stand at 20° C. for 18 hours, the solutions in the wells were then removed by suction, the wells were washed 3–4 times using 200 µl of a solution of 1 g/l ®Tween 20 in a phosphate-buffered physiological sodium chloride solution, pH 7.4, by filling and removing by suction, and the assay plates were then dried at 20° C. over silica gel.

1.2. Anti-HSV 1 and 2 IgG peroxidase conjugate

Monoclonal mouse IgG which was directed both against HSV 1 and against HSV 2 was reacted with N-gamma-maleimidobutylyloxysuccinimide (GMBS) as described by Tanamori et al., 1983 in J. Immunol. Meth. 62, 123–131. 2-Iminothiolan hydrochloride (obtained from Sigma, catalog No. I 6256) was reacted with horseradish peroxidase (POD), obtained from Messrs. Boehringer Mannheim, catalog No. 413470, as described by King et al., 1978 in Biochem. 17, 1499–1506. From the GMBS-IgG conjugate and the iminothiolan POD conjugate, an IgG-POD conjugate was prepared as described by Tanamori.

The resulting solution of the IgG-POD conjugate had a protein content of 1.2 mg/ml. The ratio of POD to IgG was determined as 2.5. The solution was subsequently diluted to 6 µg/ml of IgG-POD using a solution of 50 ml/l of fetal calf serum, 5 g/l of ®Tween 20 in PBS, and was referred to as anti-HSV-POD.

1.3. TMB substrate preparation

In order to determine anti-HSV-POD, a substrate system or substrate preparation was used which contained hydrogen peroxide and tetramethylbenzidine (TMB) and which was prepared from two stock solutions.

Stock solution 1: TMB dihydrochloride was dissolved with stirring at a concentration of 5 g/l, i.e. of 16 mmol/l in bidistilled water, and a pH of 1.5 was set using 5-normal hydrochloric acid. Penicillin G was added to this solution with stirring, at a final concentration of 200 mg/l, i.e. of 0.56 mmol/l.

Stock solution 2: 1.4 ml of glacial acetic acid, 1.5 ml of 1-normal NaOH and 250 mg, i.e. 3 mmol of $H_2O_2$ as urea/hydrogen peroxide adduct were added to 900 ml of bidistilled water. After the compounds had dissolved completely, the reaction mixture was made up to 1 l using bidistilled water.

TMB substrate preparation: one part by volume of stock solution 1 and 10 parts by volume of stock solution 2 were mixed with each other.

1.4. Procedure of the determination

150 μl portions of the previously described, HSV-containing samples which had been prepared from pustule liquid and 150 μl portions of the particular solutions used for preparation, as blank value, were filled into wells of the anti-HSV-assay plates (Example 1.1.) and were kept for 2 h in an incubator at 37° C. The content of the wells was removed by suction and the wells were washed four times using a solution of 1 g/l of ®Tween 20 in PBS, referred to as wash buffer.

100 μl of anti-HSV-POD were then transferred then into each well and incubation was carried out as previously described for 1 h at 37° C. The content of the wells was removed by suction, and the wells were washed four times using wash buffer. 100 μl of TMB substrate preparation were transferred into each well, and incubation was carried out for 30 min at 20°–220° C. and stopped by adding 100 μl of 1-normal sulfuric acid. $E_{450}$ of the colored solution was measured against a blank value of PBS.

The results are represented in the table. From this table, it can be seen that the pustule liquid shows markedly higher absorbances after treatment with the amine oxide-containing solutions than pustule liquids which had been treated with solutions of Pluronic F 68, of Tetronic 707 and of Tetronic 1107, i.e., solutions of the prior art.

TABLE

| Treatment of HSV-containing pustule liquid with solutions of the mentioned additions in PBS | | delta absorbance at 450 nm ($E_{sample} - E_{blank\ value}$) | | | |
|---|---|---|---|---|---|
| Evaluations on days | | 0 | 7 | 14 | 21 |
| Additions | | | | | |
| Amine oxide WS35 | (a) | 619 | n.t. | 644 | 653 |
| | (b) | 578 | 590 | 658 | 637 |
| Coconut dimethyl- | (a) | 661 | 582 | 577 | 611 |
| amine oxide | (b) | 721 | 577 | 547 | 554 |
| Tetradecyldimethyl- | (a) | 676 | 551 | 530 | 549 |
| amine oxide | (b) | 580 | 506 | 461 | 524 |
| Coconut bis | (a) | 688 | 629 | 581 | 565 |
| (2-hydroxyethyl)- | (b) | 646 | 560 | 605 | 419 |
| amine oxide | | | | | |
| Pluronic F 68 | (a) | 386 | | | |
| | (b) | 351 | | | |
| Tetronic 707 | (a) | 374 | | | |
| | (b) | 320 | | | |
| Tetronic 1107 | (a) | 385 | | | |
| | (b) | 336 | | | |

EXAMPLE 2

Solutions of
a) 10 g/l of N-acetyl-L-cystein
b) 1 g/l of pancreatin and c) 40 ml/l of amine oxide WS35 in PBS, containing 40 ml/l of fetal calf serum, were prepared.

Equal parts of the solutions were mixed with expectorated sputum and kept at 18° to 25° C., and pipettability was checked every 10 minutes using a 200 μl Eppendorf pipette.

It has emerged that the mixture with solution c) was pipet-table after 30 minutes and could thus be used as the sample, while the mixtures with solutions a) and b) could not yet be pipetted after the time indicated.

I claim:

1. A process for the immunochemical determination of an analyte contained in a biological material, comprising the steps of
(i) bringing into contact a sample of the biological material with an amine oxide of Formula I

where
(a) $R_1$ is a 1-alkanoyl group or a 1-alkenoyl-aminopropyl group where the alkanoyl radical or alkenoyl radical contains 8 to 18 caron atoms and $R_2$ and $R_3$ are methyl groups, ethyl groups or propyl groups, or
(b) $R_1$ is an alkyl group or an alkenyl group having 8 to 18 carbon atoms and $R_2$ and $R_3$ are methyl groups, ethyl groups or propyl groups, or
(c) $R_1$ is an alkyl group or an alkenyl group having 8 to 18 carbon atoms, $R_2$ is methyl, ethyl or propyl and $R_3$ is hydroxyethyl or hydroxypropyl, or
(d) $R_1$ is an alkyl group or an alkenyl group having 8 to 18 carbon atoms and $R_2$ and $R_3$ are hydroxyethyl or hydroxypropyl, or
(e) $R_1$ is an alkyl group or an alkenyl group having 8 to 18 carbon atoms or oxyethyl or oxypropyl or their polycondensates, $R_2$ and $R_3$ are methyl, ethyl, propyl or hydroxyethyl or hydroxypropyl, or
(f) $R_1$ is an alkanoyl group or an alkenoyl group having 8 to 18 carbon atoms or oxyethyl or oxypropyl or their polycondensates, $R_2$ and $R_3$ are methyl, ethyl, propyl or hydroxyethyl or hydroxypropyl where $R_1$, $R_2$ and $R_3$ may contain amide groups or phenol radicals to form a mixture containing 2 to 80 g/l of said amine oxide, and wherein said mixture does not contain a benzidine-type indicator;
(ii) incubating said mixture for a period of time at least necessary to liquefy the biological material, said biological material comprising tissues, blood cells, serum, plasma, secreta or excretions;
(iii) incubating said mixture or an aliquot of said mixture with a specific binding partner of said analyte, said specific binding partner being immobilized on a solid phase; and
(iv) determining the amount of said analyte being bound to said immobilized specific binding partner.

2. The process as claimed in claim 1, wherein said solid phase is a latex particle.

3. The process as claimed in claim 1, wherein said mixture contains 5 to 50 g/l of said amine oxide.

4. The process as claimed in claim 1, wherein said mixture contains 10 to 40 g/l of said amine oxide.

5. The process of claim 1 which process further comprises using a benzidine-containing indicator, and wherein said bound analyte is separated from said liquid mixture containing said amine oxide of Formula I before said benzidine-containing indicator is added.

6. The process of claim 1 wherein said determination of said bound analyte comprises the step of forming a precipitate in a dispersion or in a gel.

7. The process of claim 1 wherein said determination of said bound analyte comprises the step of producing agglutinates of particles or inhibiting the formation of such agglutinates.

8. The process of claim 1 wherein said determination of said bound analyte comprises the step of producing a color signal or preventing a color signal.

9. The process of claim 1 wherein said determination of said bound analyte comprises the step of producing or inhibiting a radiation emitted by radioisotopes, fluorescence or chemiluminescent reaction.

* * * * *